(12) United States Patent
Udipi et al.

(10) Patent No.: US 9,254,350 B2
(45) Date of Patent: Feb. 9, 2016

(54) IMPLANTABLE MEDICAL DEVICES HAVING BIOABSORBABLE PRIMER POLYMER COATINGS

(75) Inventors: Kishore Udipi, Santa Rosa, CA (US); Ya Guo, Cotati, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1480 days.

(21) Appl. No.: 12/422,018

(22) Filed: Apr. 10, 2009

(65) Prior Publication Data
US 2010/0262228 A1    Oct. 14, 2010

(51) Int. Cl.
| | | |
|---|---|---|
| *A61F 2/82* | (2013.01) | |
| *A61L 31/02* | (2006.01) | |
| *A61L 31/10* | (2006.01) | |
| *A61L 31/14* | (2006.01) | |
| *A61L 31/16* | (2006.01) | |

(52) U.S. Cl.
CPC .............. *A61L 31/022* (2013.01); *A61L 31/10* (2013.01); *A61L 31/148* (2013.01); *A61L 31/16* (2013.01); *A61L 2300/416* (2013.01); *A61L 2300/606* (2013.01)

(58) Field of Classification Search
CPC ........................................................ A61F 2/82
USPC ....................... 623/1.42–1.46, 1.49
See application file for complete search history.

(56) References Cited

U.S. PATENT DOCUMENTS

| | | | |
|---|---|---|---|
| 6,258,121 | B1 | 7/2001 | Yang et al. |
| 2003/0153971 | A1 | 8/2003 | Chandrasekaran |
| 2005/0112170 | A1 | 5/2005 | Hossainy |
| 2005/0244363 | A1 | 11/2005 | Hossainy |
| 2006/0193886 | A1 | 8/2006 | Owens |
| 2007/0050009 | A1 | 3/2007 | Flanagan |
| 2009/0004243 | A1 | 1/2009 | Pacetti |
| 2009/0118821 | A1 * | 5/2009 | Scheuermann et al. ...... 623/1.49 |
| 2010/0222875 | A1 * | 9/2010 | Pacetti .......................... 623/1.49 |

OTHER PUBLICATIONS

Int'l Search Report for Int'l App. No. PCT/US2010/026869, Jan. 24, 2011, Medtronic Vascular Inc.
"Evaluation of the In Vitro Drug Release from Resorbably Biocompatible Coatings for Vascular Stents", Sharkawa et al. *Journal of Bioactive and Compatible Polymers* 2005, vol. 20, No. 2 pp. 153-168.

* cited by examiner

*Primary Examiner* — Thomas J Sweet
*Assistant Examiner* — Matthew Schall

(57) ABSTRACT

Implantable medical devices having a metallic surface coated with a bioabsorbable primer polymer layer under a bioabsorbable drug polymer layer. Thus, in addition to the degradation of the drug polymer layer, there is degradation of the primer layer. The underlying metallic framework may or may not degrade depending on whether bioabsorbable or biostable metals are chosen.

15 Claims, No Drawings

IMPLANTABLE MEDICAL DEVICES HAVING BIOABSORBABLE PRIMER POLYMER COATINGS

FIELD OF THE INVENTION

The present disclosure generally relates to implantable medical devices having bioabsorbable primer polymer coatings.

BACKGROUND OF THE INVENTION

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury includes the expression of chemokines and adhesion molecules leading to the migration of monocytes and vascular smooth muscle cells (VSMC) from the sub endothelium into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis is reached. The balloon is then inflated restoring arterial patency. One angioplasty variation includes arterial stent deployment. Briefly, after arterial patency has been restored, the balloon is deflated and a vascular stent is inserted into the vessel lumen at the stenosis site. After expansion of the stent, the catheter is then removed from the coronary artery and the deployed stent remains implanted to prevent the newly opened artery from constricting spontaneously.

An alternative procedure involves stent deployment without prior balloon angioplasty, the expansion of the stent against the arterial wall being sufficient to open the artery, restoring arterial patency. However, balloon catheterization and/or stent deployment can result in vascular injury ultimately leading to VSMC proliferation and neointimal formation within the previously opened artery. This biological process whereby a previously opened artery becomes re-occluded is referred to as restenosis.

Stents and/or drug therapies, either alone or in combination with the percutaneous transluminal coronary angioplasty (PTCA) procedure, are often used to avoid or mitigate the effects or occurrence of restenosis. In general, stents are mechanical scaffoldings which may be inserted into a blocked or narrowed region of a passageway to provide and maintain its patency. During implantation, a stent can be positioned on a delivery device (for example and without limitation a balloon catheter) and advanced from an external location to an area of passageway blockage or narrowing within the body of the patient. Once positioned, the delivery device can be actuated to deploy the radially expandable stent. Expansion of the stent can result in the application of force against the internal wall of the passageway, thereby improving the patency of the passageway. Thereafter, the delivery device can be removed from the patient's body.

Stents may be manufactured in a variety of lengths and diameters and from a variety of materials ranging from metallic materials to polymers. Stents may also incorporate and release drugs (i.e., "drug-eluting stents") that can affect endothelialization as well as the formation of and treatment of existing plaque and/or blood clots. In some instances then, drug-eluting stents can reduce, or in some cases, eliminate, the incidence of endothelialization, thrombosis and/or restenosis.

Additionally, recent advances in in situ drug delivery has led to the development of implantable medical devices specifically designed to provide therapeutic compositions to remote anatomical locations. Perhaps one of the most exciting areas of in situ drug delivery is in the field of intervention cardiology. Vascular occlusions leading to ischemic heart disease are frequently treated using percutaneous transluminal coronary angioplasty (PTCA) whereby a dilation catheter is inserted through a femoral artery incision and directed to the site of the vascular occlusion. The catheter is dilated and the expanding catheter tip (the balloon) opens the occluded artery restoring vascular patency. Generally, a vascular stent is deployed at the treatment site to minimize vascular recoil and restenosis. However, in some cases stent deployment leads to damage to the intimal lining of the artery which may result in vascular smooth muscle cell hyperproliferation and restenosis. When restenosis occurs it is necessary to either re-dilate the artery at the treatment site, or, if that is not possible, a surgical coronary artery bypass procedure must be performed.

Implantable medical devices have become increasingly more common over the last fifty years and have found applications in nearly every branch of medicine. Examples include joint replacements, vascular grafts, heart valves, ocular lenses, pacemakers, vascular stents, urethral stents, and many others. However, regardless of the application, implantable medical devices must be biocompatible. They must be fabricated from materials that will not elicit an adverse biological response such as, but not limited to, inflammation, thrombogensis or necrosis. Thus, early medical devices were generally fabricated from inert materials such as precious metals and ceramics. More recently, stainless steel and other metal alloys have replaced precious metals and polymers are being substituted for ceramics.

Recently, it has been determined that drug-eluting stents coated with anti-proliferative drugs such as, but not limited to, rapamycin and its analogs and paclitaxel have shown great promises in preventing restenosis. However, there is a need to develop additional and potentially more efficacious drug-eluting stents (DES). One critical factor in DES efficacy is the drug elution rate. Drug elution is generally a factor of the drug's solubility in the polymer coating applied to the stent.

One of the critical components of a drug eluting stent is the polymer coating material. The coating material serves as the reservoir from which drug release is controlled. After all of the drug has bee released or depleted, the polymeric coating may serve as a permanent implant material. For the success of a permanent implant, the coating must be biocompatible. Under certain circumstances it is also desirable that the polymeric coating be bioabsorbable.

Problems have been encountered with polymers which are used to carry one or more drugs to be released from a medical device such as a vascular stent because they do not adhere strongly to a metallic surface of a medical device. Therefore, a primer or adhesive coating layer is often used under a drug polymer coating for better adhesion to a metallic medical device surface. However, if complete degradation of the polymer coatings is sought, the primer layer must be bioabsorbable. Thus, there is a need for biodegradable polymers which may serve as primer coatings or layers on implantable medical devices such as vascular stents.

SUMMARY OF THE INVENTION

The present bioabsorbable primer polymers provide associated implantable medical devices the possibility of complete bioabsorbability or biodegradability of polymer coating(s). One or more coatings having the present bioabsorbable primer polymers degrade in addition to the bioabsorbable or biodegradable drug polymer layer(s) provided on an implantable medical device having a metallic framework. The bioabsorbable primer polymers increase the strength of adhesion between the surface of the metallic framework and one or more bioabsorbable drug polymer layers provided on the metallic framework of an implantable medical device.

Therefore, in one embodiment, the present disclosure relates to an implantable medical device comprising a metallic framework; a coating comprising a bioabsorbable primer polymer located on top of and in contact with the metallic framework; a drug-polymer bioabsorbable coating comprising at least one drug and a bioabsorbable polymer located on top of and in contact with the bioabsorbable primer polymer coating; and wherein the bioabsorbable primer polymer has a molecular weight that is less than or equal to about 50,000 g/mol.

In another embodiment of the implantable medical device, the bioabsorbable primer polymer comprises one or more monomers selected from the group consisting of L-lactide, DL-lactide, caprolactone, glycolide, and gamma-butylactone.

In another embodiment of the implantable medical device, the bioabsorbable primer polymer is a homopolymer. In another embodiment of the implantable medical device, the bioabsorbable primer polymer is a copolymer.

In another embodiment of the implantable medical device, the bioabsorbable primer polymer is poly(DL-lactide-co-caprolactone).

In another embodiment of the implantable medical device, the bioabsorbable polymer of the drug polymer bioabsorbable coating is selected from the group consisting of L-lactide, DL-lactide, caprolactone, caprolactone derivatives, tirmethylene carbonate, and gamma-butyroactone; and wherein the bioabsorbable polymer of the drug polymer bioabsorbable coating has a molecular weight that is greater than about 50,000 g/mol.

In another embodiment of the implantable medical device, the drug is selected from the group consisting of rapamycin, rapamycin derivatives such as zotarolimus or everolimus, paclitaxel, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof.

In another embodiment of the implantable medical device, the drug is rapamycin or a rapamycin derivative.

In another embodiment of the implantable medical device, the implantable device is selected from the group consisting of a vascular stent, stent graft, bone screw, and bone anchor.

In another embodiment of the implantable medical device, the implantable device is a vascular stent.

In another embodiment of the implantable medical device, the metallic framework of the implantable medical device is biostable.

In another embodiment of the implantable medical device, the metallic framework of the implantable medical device is bioabsorbable.

In another embodiment of the implantable medical device, the metallic framework comprises a metal selected from the group consisting of stainless steel, nitinol, tantalum, a non-magnetic nickel-cobalt-chromium-molybdenum [MP35N] alloy, platinum, titanium, and a combination thereof.

In another embodiment of the implantable medical device, the metallic framework comprises a magnesium alloy, an iron alloy; or a combination thereof.

The present disclosure also relates to a vascular stent comprising a magnesium or iron metallic framework, a coating comprising a bioabsorbable primer polymer comprising poly(DL-lactide-co-caprolactone) located on top of and in contact with the metal framework, a drug-polymer bioabsorbable coating comprising rapamycin or a rapamycin derivative and a bioabsorbable polymer located on top of and in contact with the bioabsorbable primer polymer coating, and wherein the bioabsorbable primer polymer has a molecular weight less than or equal to about 50,000 g/mol.

DETAILED DESCRIPTION OF THE INVENTION

Despite the development of metallic stents, they continue to have limitations such as stent thrombosis, which requires prolonged antiplatelet therapy, and mismatch of the stent to the vessel size, which often results in a smaller lumen after stent implantation. Further, metallic stents prevent the lumen expansion associated with late favorable remodeling. Permanent metallic stents impair the vessel geometry and often jail and obstruct side branches. Drug-eluting stents were a breakthrough in the development of stents, with their ability to significantly reduce restenosis rates and the need for repeat revascularization. Nevertheless, they are still associated with subacute and late thrombosis, and necessitate prolonged antiplatelet therapy for at least 12 months. Further, polymers used as a vehicle for drug delivery may induce vessel irritation, endothelial dysfunction, vessel hypersensitivity and chronic inflammation at the stent site. Excessive use of stents in the coronary vasculature (full metal jacket) may interfere with traditional reinterventional techniques such as bypass graft surgery. Finally, metallic stents pose artifacts with modern imaging technologies such as magnetic resonance imaging (MRI) and multislice computerized tomography (MSCT), which eventually will become the default noninvasive imaging modality for the coronary anatomy.

In contrast, bioabsorbable stents, once they are bioabsorbed, leave behind only the healed natural vessel, allowing restoration of vasoreactivity with the potential of vessel remodeling. Late stent thrombosis is unlikely since the stent is gone, and prolonged antiplatelet therapy is not necessary in this instance. Bioabsorbable stents can also be suitable for complex anatomy where stents impede on vessel geometry and morphology and are prone to crushing and fractures, such as is seen in saphenous femoral and tibial arteries. Bioabsorbable implant stents can be used as a delivery device for agents such as drugs and genes, and will perhaps play a role in the treatment of vulnerable plaque. Transferring genes that code key regulatory pathways of cell proliferation inside the cells of the arterial wall using polymer stents as vehicles is feasible. Regardless of which agent (drug or gene) will finally conquer restenosis, a polymer stent remains an optional vehicle for such delivery. Finally, bioabsorbable stents are compatible with MRI and MSCT imaging.

Metal bioabsorbable stents are attractive since they have the potential to perform similarly to stainless steel metal stents. So far, two bioabsorbable metal alloys have been proposed for this application: alloys of magnesium and alloys of iron. The biocompatibility of these stents depends on their solubility and their released degradation products. Their local toxicity is related to the local concentration of the elements over time. The tissue tolerance for physiologically occurring metals depends on the change of their tissue concentrations induced by corrosion. Thus, metals with high tissue concentrations are the ideal candidates for bioabsorbable stents.

When using one or more metals to fashion a bioabsorbable stent, a primer or adhesive coating layer may be needed to better adhere a polymer layer containing an elution drug to the metal framework. For a bare metal stent, parylene has been used to first coat the metal stent framework before applying a drug/polymer layer. With the advent of bioabsorbable metals, which may serve as a stent framework, it is desirable to have a primer or adhesive layer which also is biodegradable. When the metal framework, drug polymer layer and the primer or adhesive layers are all biodegradable, the entire implantable medical device such as a vascular stent may have to be fully bioabsorbable.

Therefore, the present disclosure relates to an implantable medical device comprising a metallic framework, a coating comprising a bioabsorbable primer polymer located on top of and in contact with the metallic framework, a drug-polymer bioabsorbable coating comprising a drug and a bioabsorbable polymer located on top of and in contact with the bioabsorbable primer polymer coating; wherein the bioabsorbable primer polymer has a molecular weight that is less than or equal to about 50,000 g/mol, less than or equal to about 20,000 g/mol, less than or equal to about 10,000 g/mol, less than equal to about 8,000 g/mol, less than equal to about 6000 g/mol, less than or equal to about 4,000 g/mol, or less than equal to about 2,000 g/mol.

A monomer is a small molecule that can become chemically bonded to other monomers to form a polymer. A polymer is a large molecule (macromolecule) composed of repeating structural units typically connected by covalent chemical bonds. As used herein a "copolymer" will be defined as a macromolecule produced by the simultaneous or step-wise polymerization of two or more dissimilar units such as monomers. Copolymer shall include bipolymers (two dissimilar units), terpolymer (three dissimilar units), etc. In one embodiment, the present bioabsorbable primer polymer is a copolymer. Further, as used herein, "homopolymer" shall mean a polymer being composed of a single monomer. In one embodiment, the present bioabsorbable primer polymer is a homopolymer.

In one embodiment of the present implantable device, the bioabsorbable primer polymer of the present disclosure comprises one or more monomers selected from the group consisting of L-lactide, DL-lactide, caprolactone, glycolide, and gamma-butylactone. The primer polymers formed from the monomers may be homopolymers or copolymers. A preferred bioabsorbable primer polymer is poly(DL-lactide-co-caprolactone).

The drug polymer coating will have at least one polymer which is made of at least two monomers. By varying the amount of monomers used as well the reaction conditions the properties of the polymers can be fine tuned for drug delivery, more specifically, controlled drug release rates. The polymers of the drug polymer coating in accordance with the present disclosure are suitable for the controlled release of both hydrophobic and hydrophilic drugs, either independently or in combination. As used herein in reference to the bioactive agent or drugs, "hydrophilic" refers to a bioactive agent that has a solubility in water of more than 200 micrograms per milliliter. As used herein in reference to the bioactive agent or drug the term "hydrophobic" refers to a bioactive agent that has a solubility in water of no more than 200 micrograms per milliliter.

As used herein "controlled release" refers to the release of a drug from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is release in even amounts over a predetermined time (with or without an initial burst phase) or may be a gradient release. A gradient release implies that the concentration of drug released from the device surface changes over time.

Controlling drug release rates from the polymers of the drug polymer coating of the present disclosure requires adjusting the properties of the polymers. One non-limiting method of controlling drug release rates in the polymers of the present disclosure involves controlling the glass transition temperature (Tg) of the polymers. As used herein, glass transition temperature (Tg) refers to a temperature wherein a polymer structurally transitions from an elastic pliable state to a rigid and brittle state.

In accordance with the scope and teachings of the present disclosure, bioabsorbable polymers of the drug polymer bioabsorbable coatings of the present implantable device may be, for example, selected from the group consisting of polyesters such as polylactide, poylglycolide, polycaprolactone, and their copolymers, modified derivatives of caprolactone polymers, polytrimethylene carbonate, and polysaccharides, polyethylene glycol, hydrogels, photo-curable hydrogels, terminal diols, and combinations thereof The bioabsorbable polymer of the drug polymer bioabsorbable coating has a molecular weight that is greater than the molecular weight of the bioabsorbable primer polymer. The bioabsorbable polymer of the drug polymer bioabsorbabe coating thus has greater mechanical strength than the instant bioabsorbable primer polymers due in part to it's higher molecular weight and selection of monomers. Further, the bioabsorbable polymers of the drug polymer coating may be homopolymers or copolymers.

The present bioabsorbable primer polymers of the associated implantable medical device have a molecular weight that is less than or equal to about 50,000 g/mol. This lower molecular weight gives the bioabsorbable primer polymer its adhesive property.

The drug polymer coatings are intended for medical devices deployed in a hemodynamic environment and possess excellent adhesive properties. That is, the coating must be stably adhered to the medical device surface. Many different materials can be used to fabricate the substrate or metallic framework of implantable medical devices including, but not limited to, magnesium or iron, stainless steel, nitinol, aluminum, chromium, titanium, gold, cobalt, and alloys and combinations thereof. All of these materials, and others, may be used with the polymeric coatings made in accordance with the teachings of the present disclosure.

There are many theories that attempt to explain or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The biodegradable polymeric coatings used for primer coatings and drug polymer coatings of the present disclosure can be applied to medical device surfaces in any manner known to those of ordinary skill in the art. Application methods compatible with the present invention include, but are not limited to, spraying, dipping, brushing, vacuum-deposition, and others. Moreover, the drug polymeric coatings of the present invention may be used with a cap coat. A cap coat as used herein refers to the outermost coating layer applied over another coating. A drug-polymer coating of the present disclosure is applied over the primer coat. Then, a polymer cap coat is applied over the polymeric coating of the present disclosure. The cap coat may optionally serve as a diffusion barrier to control drug release. The cap coat may be merely a biocompatible polymer applied to the surface of the sent to protect the stent and have no effect on the bioactive agent release rates. In a preferred embodiment, the cap coat is also bioabsorbable.

The polymers of the drug polymer coating are useful for the delivery and controlled release of drugs. Drugs that are suitable for release from the polymers of the present invention include, but are not limited to, rapamycin, rapamycin derivatives such as zotarolimus and everolimus, paclitaxel, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof.

Bioabsorbable polymers are utilized in accordance with various embodiments of the present invention. As used herein, "bioabsorbable polymer" refers to a polymer or copolymer which is absorbed by the body Bioabsorbable polymers for use herein should be biocompatible.

In accordance with the scope and teachings of the present disclosure, the implantable medical devices can be, but are not limited to, vascular stent, stent graft, bone screw and bone anchor. In one embodiment, the entire implantable medical device is bioabsorbable. The underlying stent framework, adhesive or primer layer, and the drug polymer coating are all bioabsorbable in this embodiment. This is possible when the underlying substrate or metal framework also is bioabsorbable. The two metals which may serve as the metal frame work and which are biodegradable are magenisium and iron. An alloy of magenisum and iron is also within the scope and teachings of the present disclosure.

Magnesium and its alloys are biocompatible, bioabsorbable and easy to mechanically manipulate presenting an attractive solution for reinforcing bioabsorbable polymer stents. Radiological advantages of magnesium include compatibility with magnetic resonance imaging (MRI), magnetic resonance angiography and computed tomography (CT). Vascular stents comprising magnesium and its alloys are less thrombogenic than other bare metal stents. The biocompatibility of magnesium and its alloys stems from its relative non-toxicity to cells. Magnesium is abundant in tissues of animals and plants, specifically magnesium is the fourth most abundant metal ion in cells, the most abundant free divalent ion and therefore is deeply and intrinsically woven into cellular metabolism. Magnesium-dependent enzymes appear in virtually every metabolic pathway is also used as a signaling molecule. In one embodiment, the magnesium alloy comprises between about 1% and about 10% aluminum and between about 0.5% and about 5% zinc.

The magnesium alloys of the present description include but are not limited to Sumitomo Electronic Industries (SEI, Osaka, Japan) magnesium alloys AZ31 (3% aluminum, 1% zinc and 96% magnesium) and AZ61 (6% aluminum, 1% zinc and 93% magnesium). The main features of the alloy include high tensile strength and responsive ductility. Tensile strength of typical AZ31 alloy is at least 280 MPa while that of AZ61 alloy is at least 330 MPa.

A specific preferred embodiment of the implantable device of the present disclosure is a vascular stent comprising a magnesium or iron metallic framework; a coating comprising a bioabsorbable primer polymer comprising poly(DL-lactide-co-caprolactone) located on top of and in contact with the metal framework; a drug-polymer bioabsorbable coating comprising rapamycin or a rapamycin derivative and a bioabsorbable polymer located on top of and in contact with the bioabsorbable primer polymer coating; and wherein the bioabsorbable primer polymer has a molecular weight less than or equal to about 50,000 g/mol.

When full bioabsorbability of the entire implantable medical device, such as a vascular stent, is not required, an implantable medical device may comprise, for example, a non-biodegradable metallic material such as stainless steel, nitinol, tantalum, a nonmagnetic cobalt-chromium alloy such as MP35N, platinum, titanium, or alloys and combinations thereof.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An implantable medical device comprising:
a metallic framework;
a coating comprising a bioabsorbable primer polymer located on top of and in contact with said metallic framework;
a drug-polymer bioabsorbable coating comprising a drug and a bioabsorbable polymer located on top of and in contact with said bioabsorbable primer polymer coating; and
wherein said bioabsorbable primer polymer has a molecular weight that is less than or equal to about 50,000 g/mol.

2. The implantable medical device of claim 1, wherein said bioabsorbable primer polymer comprises one or more monomers selected from the group consisting of L-lactide, DL-lactide, caprolactone, glycolide, and gamma-butylactone.

3. The implantable medical device of claim 1, wherein said bioabsorbable primer polymer is a homopolymer.

4. The implantable medical device of claim 1, wherein said bioabsorbable primer polymer is a copolymer.

5. The implantable medical device of claim 1, wherein said bioabsorbable primer polymer is poly(DL-lactide-co-caprolactone).

6. The implantable medical device of claim 1, wherein said bioabsorbable polymer of said drug polymer bioabsorbable coating is selected from the group consisting of L-lactide, DL-lactide, caprolactone, caprolactone derivatives, tirmethylene carbonate, and gamma-butylactone.

7. The implantable medical device of claim 1, wherein said drug is selected from the group consisting of rapamycin, rapamycin derivatives, paclitaxel, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and combinations thereof.

8. The implantable medical device of claim 1, wherein said drug is rapamycin or its derivatives.

9. The implantable medical device of claim 1, wherein said implantable medical device is selected from the group consisting of a vascular stent, stent graft, bone screw, and bone anchor.

10. The implantable medical device of claim 1, wherein said implantable medical device is a vascular stent.

11. The implantable medical device of claim 1, wherein said metallic framework of said implantable medical device is biostable.

12. The implantable medical device of claim 1, wherein said metallic framework of said implantable medical device is bioabsorbable.

13. The implantable medical device of claim 11, wherein said metallic framework comprises a metal selected from the group consisting of stainless steel, nitinol, tantalum, a non-magnetic cobalt-chromium [MP35N] alloy, platinum, titanium, and alloys and combinations thereof.

14. The implantable medical device of claim 12, wherein said metallic framework comprises magnesium or iron; or alloys and combinations thereof.

15. A vascular stent comprising:
a metallic framework comprising magnesium or iron;
a coating comprising a bioabsorbable primer polymer comprising poly(DL-lactide-co-caprolactone) located on top of and in contact with said metal framework;
a drug-polymer bioabsorbable coating comprising rapamycin or a rapamycin derivative and a bioabsorbable polymer located on top of and in contact with said bioabsorbable primer polymer coating; and
wherein said bioabsorbable primer polymer has a molecular weight less than or equal to about 50,000 g/mol.

* * * * *